United States Patent [19]

Houminer et al.

[11] Patent Number: 5,080,719

[45] Date of Patent: Jan. 14, 1992

[54] SMOKING COMPOSITIONS CONTAINING A HETEROAROMATIC FLAVORANT-RELEASE ADDITIVE

[75] Inventors: Yoram Houminer, Jerusalem, Israel; Henry V. Secor, Midlothian; Jeffrey I. Seeman, Richmond, both of Va.

[73] Assignee: Philip Morris Incorporated, New York, N.Y.

[21] Appl. No.: 100,694

[22] Filed: Sep. 24, 1987

[51] Int. Cl.⁵ .............................. A24B 3/12
[52] U.S. Cl. .................... 131/278; 546/348; 546/349
[58] Field of Search ............ 131/276, 278; 546/348, 546/349, 350

Primary Examiner—V. Millin
Attorney, Agent, or Firm—Arthur I. Palmer; James E. Schardt

[57] ABSTRACT

This invention privdes novel heteroaromatic compounds, and smoking compositions which contain an invention heteroaromatic compound as a flavorant-release additive as illustrated by the following additive structure:

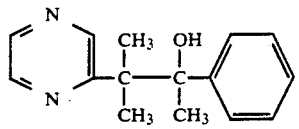

Under typical cigarette smoking conditions, 2-isopropylpyrazine and acetophenone are released as pyrolysis products, and enhance the flavor and aroma of the mainstream and sidestream smoke.

18 Claims, No Drawings

SMOKING COMPOSITIONS CONTAINING A HETEROAROMATIC FLAVORANT-RELEASE ADDITIVE

BACKGROUND OF THE INVENTION

It has been established that alkylpyrazines are natural components of tobacco smoke, and are contributors to tobacco smoke flavor [A. Baggett et al J. Chromatog, 97, 79 (1974)]. Further, it has been disclosed in the patent literature that addition of alkyl pyrazines to tobacco results in an improvement in the flavor of smoking compositions as perceived by a test panel.

U.S. Pat. No. 3,402,051 describes a process for imparting a popcorn-like flavor and aroma to tobacco and foodstuffs by the incorporation of a 2-acetylpyrazine derivative therein.

Other patents which disclose the addition of various pyrazine compounds to tobacco and foodstuffs as a means of providing flavor or flavor enhancement include U.S. Pat. Nos. 3,684,809; 3,705,158; 3,754,934; 3,764,349; 3,767,426; and 3,881,025.

U.S. Pat. No. 3,914,227 discloses pyridyl and pyrazyl ketones and their use in altering the organoleptic properties of tobacco and foodstuffs, and U.S. Pat. No. 4,166,869 discloses acylpyrimidines useful as flavorants for the same type of applications.

Alkylpyridines have also been found to be useful tobacco additives. As an example, U.S. Pat. No. 3,625,224 describes the use of methylpyridines, ethylpyridines and various dialkylpyridines as tobacco additives. U.S. Pat. No. 3,381,691 discloses 2-methyl-5-isopropylpyridine as a tobacco additive.

It is characteristic of pyridine, pyrazine, pyrimidine and other heterocyclic derivatives employed as tobacco flavorants in the prior art, as illustrated by the above described technical literature, that the respective heterocyclic derivatives have the disadvantage of both high volatility and low odor threshold. Both of these properties significantly restrict the extent that these heterocyclic derivatives can be utilized as flavorants in tobacco compositions. A quantity of a pyrazine or pyridine derivative in a tobacco composition sufficient to have a noticeable effect in low delivery cigarettes causes a marked pack aroma.

U.S. Pat. No. 4,036,237 endeavors to overcome some of the disadvantages of the above-described flavorant technology. The said patent provides for the incorporation in smoking compositions of a flavorant compound which imparts cherry-like or fruity flavor to the smoke thereof, which flavorant compound is not lost during the manufacture and storage of the flavored smoking composition, and which is readily released when the smoking composition is burned. Illustrative of a U.S. Pat. No. 4,036,237 flavorant compound is ethyl 2,2-dimethyl-3-hydroxy-3phenylpropionate.

U.S. Pat. No. 4,259,969 describes smoking flavorant-release additives such as 2,3-dihydroxy-2,3-dimethyl-1,4-bis(3,5,6-trimethyl-2 pyrazinyl)butane. Under smoking conditions there are released substituted-pyrazine pyrolysis products which enhance the flavor of the mainstream smoke and improve the aroma of the sidestream smoke.

U.S. Pat. No. 4,312,368 and related U.S. Pat. No. 4,479,003 describe heterocyclic-hydroxy-substituted alkanoate flavorant additives such as ethyl 2-(2-butyl)-3-hydroxy-3-methyl-3-(3-pyridyl)propionate:

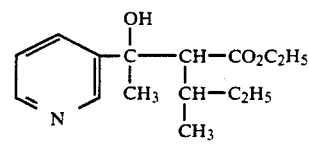

Under normal smoking conditions the favorant additive pyrolyzes into components which contribute enhanced flavor and aroma to the smoke streams.

U.S. Pat. No. 4,171,214 is of general interest as disclosing pyrazine intermediates which are related structurally to the present invention smoking composition additives.

There is continuing research effort to develop improved smoking compositions which contain a new and efficient low volatility flavorant-release additive, and which generate mainstream smoke with flavorant-enhanced taste and character under smoking conditions.

Accordingly, it is an object of this invention to provide smoking compositions having incorporated therein a flavorant component which is characterized by lack of mobility and/or volatility at ambient temperature.

It is another object of this invention to provide smoking compositions having incorporated therein a flavorant-release additive which under normal smoking conditions yields pyrolysis constituents which impart improved flavorant properties to mainstream and sidestream smoke.

It is a further object of this invention to provide novel heteroaromatic compounds of low volatility which are adapted to be incorporated into cigarette fillers, and which under normal smoking conditions release volatile alkylpyrazine and other flavorant constituents into cigarette smoke.

Other objects and advantages of the present invention shall become apparent from the following description and examples.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.0001–5 weight percent, based on the total weight of filler, of a novel flavorant-release additive corresponding to the formula:

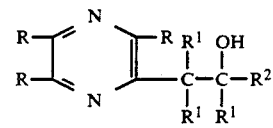

where R is hydrogen or a $C_1$–$C_4$ alkyl group: $R^1$ is hydrogen or a $C_1$–$C_8$ alkyl group; and $R^2$ is a $C_3$–$C_{12}$ aromatic substituent; with the proviso that at least two $R^1$ groups are $C_1$–$C_8$ alkyl groups.

Illustrative of the R substituent are hydrogen, methyl, ethyl, propyl, butyl, isobutyl and 2-butyl radicals.

Illustrative of the $R^1$ substituent are R type of alkyl groups, and additionally can be selected from higher alkyl radicals such as pentyl, 2-pentyl, hexyl, 2-hexyl, heptyl, octyl, isooctyl, and the like.

Illustrative of the $R^2$ substituents are substituted and unsubstituted aromatic structures such as phenyl, methoxyphenyl, tolyl, xylyl, naphthyl, and the like, and heteroaromatic structures such as substituted and unsubstituted pyridyl, methylpyridyl, pyrazyl, thiazyl, furyl, and thienyl monovalent radicals.

The preferred $R^2$ substituents are substituted and unsubstituted phenyl, pyridyl and pyrazyl monovalent radicals.

In another embodiment this invention provides a novel pyrazine composition corresponding to the

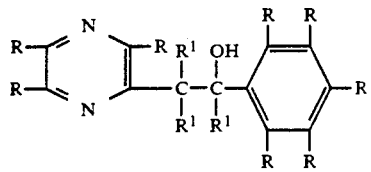

where R is hydrogen or a $C_1$-$C_4$ alkyl group; and $R^1$ is hydrogen or a $C_1$-$C_8$ alkyl group; with the proviso that at least two $R^1$ groups are $C_1$-$C_8$ alkyl radicals.

When a present invention smoking composition is subjected to normal smoking conditions, the low volatility heteroaromatic additive pyrolyzes into volatile components which enhance the flavor and aroma of low delivery cigarette smoke:

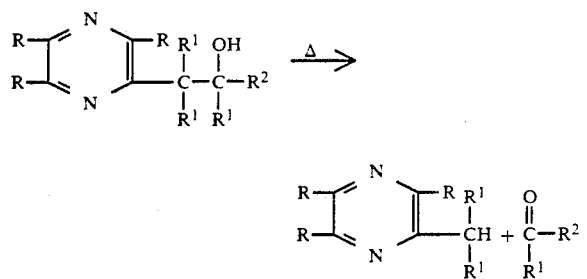

The present invention heteroaromatic flavorant-release additives are stable and odorless compounds at ambient temperature. In addition, the additives decompose at a relatively low pyrolysis temperature (e.g., 150°–300°) to release a high yield of desirable flavor-enhancing heteroaromatic and carbonyl components in mainstream smoke.

Preparation Of Heteroaromatic Compounds

A general procedure for the preparation of present invention heteroaromatic flavorant-release compounds involves the reaction of a selected alkylpyrazine anion with a carbonyl derivative in a solvent medium:

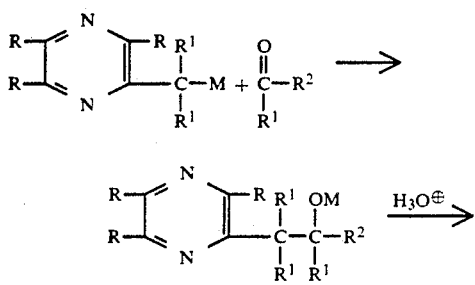

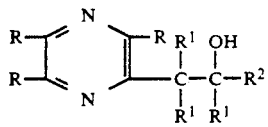

where M is a metal atom such as lithium, and R, $R^1$ and $R_2$ are as previously defined.

An alternative procedure is preferred for the synthesis of a compound such as (R,S)-2-(1,1-dimethyl-2-hydroxy-2-phenylethyl)pyrazine in which steric hindrance by substituents is a factor:

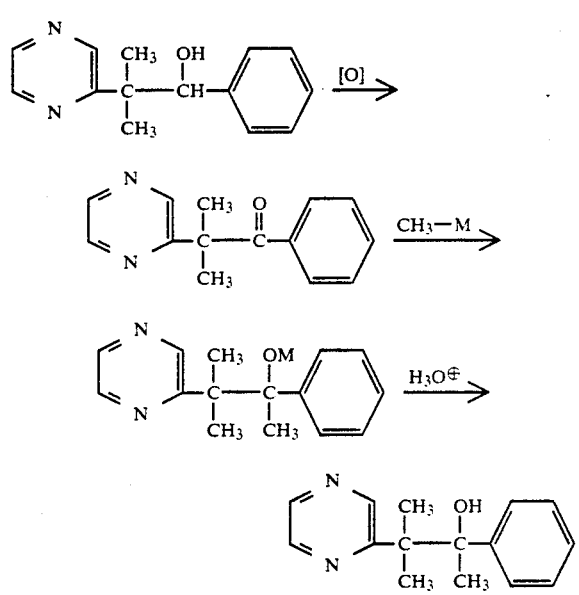

Preparation of Smoking Compositions

In a further embodiment this invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.0001–5 weight percent, based on composition weight, of a flavorant-release additive corresponding to the formula:

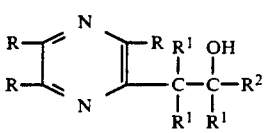

where R is hydrogen or a $C_1$-$C_8$ alkyl group; $R^1$ is hydrogen or a $C_1$-$C_8$ alkyl group; and $R^2$ is a $C_3$-$C_{12}$ aromatic substituent; with the proviso that at least two $R^1$ groups are $C_1$-$C_8$ alkyl radicals.

The invention flavorant-release additive can be incorporated into the tobacco or tobacco substitute in accordance with methods known and used in the art. Preferably the flavorant-release additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco and/or tobacco substitute filler in a concentration between about 0.5–5 weight percent, based on the weight of filler, and then subsequently to blend the treated filler with filler which does not contain flavorant additive.

The term "tobacco substitute" is meant to include non-tobacco smoking filler materials such as are disclosed in U.S. Pat. Nos. 3,703,177; 3,796,222; 4,019,521; 4,079,742; and references cited therein; incorporated herein by reference.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

The following Examples are further illustrative of the present invention. The specific ingredients and processing parameters are presented as being typical, and various modifications can be derived in view of the foregoing disclosure within the scope of the invention.

EXAMPLE I

Preparation of
(R,S)-2-(2-Hydroxy-2-phenylethyl)-3-methylpyrazine

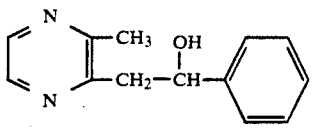

A solution of diisopropylamine (22.2 g, 0.22 mole) in ether (500 ml) is stirred under nitrogen atmosphere and treated with n-BuLi (0.20 mole) in hexane (119 ml) at −75° C. The resulting solution is warmed to 0° C. and a solution of 2,3-dimethylpyrazine (21.6 g, 0.20 mole) in ether (30 ml) is added slowly and the reaction mixture is stirred at 0° C. for 30 minutes.

A solution of benzaldehyde (21.2 g, 0.20 mole) in ether (30 ml) is added and stirring at 0° C. is continued for an additional 30 minutes. Water is added to the reaction medium then the organic layer is separated, washed with water, and dried over $Na_2SO_4$.

Evaporation of the solvent under reduced pressure provides an orange colored oil which is distilled bulb-to-bulb [155°–165° C. (oven), 0.02 mm Hg] to give 22.2 of a light yellow colored oil which crystallizes on standing. Recrystallization of the crude product from ether yields 13.84 g (32.3%) of product: mp 85° –86° C.; $^1$H NMR ($CDCl_3$) δ 2.47 (s, 3H), 3.14 (m, 2H), 4.83 (d, 2H, J = 2.9 Hz), 5.30 (m, 1H), 7.27–7.45 (m, 5H), 8.35 (q, 2H, J = 2.7 Hz).

Anal. Calc. for $C_{13}H_{14}N_2O$: C,72.87; H,6.59; N,13.08. Found: C,73.19; H,6.88; N,13.09.

EXAMPLE II

Preparation Of
(R,S)-2-(2-Hydroxy-2-phenylethyl)-3-ethylpyrazine

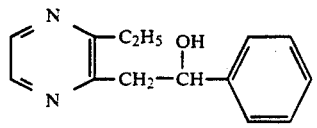

A reaction of 2-ethyl-3-methylpyrazine (12.2 g, 0.01 mole) with benzaldehyde (10.6 g, 0.1 mole) is conducted in accordance with the procedure of Example I. Workup followed by bulb-to-bulb distillation (155° C. oven/0.02 mm Hg) provides 18.2 g of a light yellow colored oil. This material crystallizes on trituration with hexane, giving 17.80 g (78%) of desired product, mp 52°–53° C.

An analytical sample is obtained by recrystallization from hexane: mp 53°–54° C.; $^1$H NMR ($CDCl_3$) δ 1.25 (t, 3H, J = 7.4 Hz), 2.77 (q, 2H, J = 7.4 Hz), 3.16 (d, 2H, J = 6.2 Hz), 5.01 (d, 1H, J = 2.5 Hz), 5.28 (m, 1H), 7.27–7.46 (m, 5H), 8.33 (d, 1H, J = 2.8 Hz), 8.40 (d, 1H, J = 2.8 Hz).

Anal. Calc. for $C_{14}H_{16}N_2O$: C,73.65; H,7.06; N,12.27. Found: C,73.73; H,7.01; N,12.31.

EXAMPLE III

Preparation Of
(R,S)-2-(2-Hydroxy-2-phenylethyl)-3-isopropylpyrazine

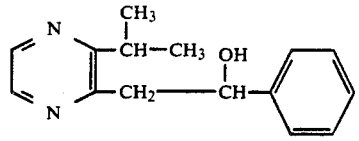

A reaction of 2-isopropyl-3-methylpyrazine (0.62 g, 4.56 mmoles) with benzaldehyde (0.48 g, 4.56 mmoles) is conducted in accordance with the procedure of Example I. Workup followed by bulb-to-bulb distillation [100° –135° C. (oven), 0.01 mm Hg] provides 800 mg of a yellow-orange colored oil. The material is chromatographed on silica gel using 199:1 $CHCl_3$/EtOH to give 386 (34.9%) of a colorless oil product which crystallizes below room temperature: $^1$H NMR ($CDCl_3$ ) δ1.20,1.21, 1.24, 1.26 (two doublets, 6, diastereotopic isopropyl methyl signals), 3.15–3.27 (m, 3H), 5.02 (d, 1H, J = 2.6 Hz), 5.3 (m, 1H), 7.28–7.50 (m, 5H), 8.35 (d, 1H, J = 2.4 Hz), 8.47 (d, 1H, J = 2.4 Hz).

Anal. Calc. for $C_{15}H_{18}N_2O$: C,74.35; H,7.49; N,11.56. Found C,74.16; H,7.35; N,11.33.

EXAMPLE IV

Preparation Of (R,S) 2-(2-Hydroxy-2-phenylethyl)-3-isobutylpyrazine

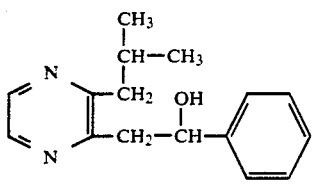

A reaction of 2-isopropyl-3-methylpyrazine (3.0 g, 20 mmoles) with benzaldehyde (2.12 g, 20 mmoles) is conducted in accordance with the procedure of Example I. Standard workup is followed by bulb-to-bulb distillation [153° C. (oven), 0.005 mm Hg]. The resulting oil crystallizes on trituration with hexane to yield 2.5 g (48.8%) of the desired product; mp 52°-53° C.; $^1$H NMR (CDCl$_3$) δ 0.92 (d, 3H, J = 6.7 Hz), 2.0-2.2 (m, 1H), 2.62-2.64 (m, 2H), 3.17 (m, 2H), 5.24-5.28 (m, 1H), 7.25-7.45 (m, 5H), 8.34 (d, 1H, J = 2.5 Hz), 8.43 (d, 1H, J = 2.5 Hz).

Anal. Calc. for C$_{16}$H$_{20}$N$_2$O: C,74.96; H,7.86; N,10.93. Found: C,75.20; H,7.73; N,10.87.

EXAMPLE V

Preparation of (R,S)-2-(2-Hydroxy-2-phenylethyl)-3-tert.-butylpyrazine

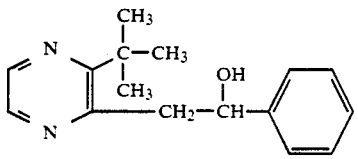

A reaction of 2-tert.-butyl-3-methylpyrazine (0.89 g, 5.95 mmoles) with benzaldehyde (b 0.63 g, 5.95 mmoles) is conducted in accordance with the procedure of Example I. Standard workup is followed by bulb-to-bulb distillation [up to 100° C. (oven), 0.025 mm Hg]. Centrifugal chromatography of the residual fraction using silica gel and 85:15 hexanes/acetone is followed by bulb-to-bulb distillation [150° C. (oven), 0.01 mm Hg] and recrystallization from hexane to yield 0.643 g (42%) of the desired product: mp 89°-90° C.; $^1$H NMR (CDCl$_3$) δ 1.44 (s, 9H), 3.25 (dd, 1H, J = 16.0, 9.5 Hz), 3.50 (dd, 1H, J = 16.0, 2.2 Hz), 5.23 (br d, 1H, J = 9.0 Hz), 5.78 (s, 1H), 7.30-7.52 (m, 5H), 8.38 (d, 1H, J = 2.2 Hz), 8.47 (d, 1H, J = 2.2 Hz).

Anal. Calc. for C$_{16}$H$_{20}$N$_2$O: C,74.96; H,7.86; N,10.93. Found: C,74.83; H,7.98; N,10.88.

EXAMPLE VI

Preparation Of (1RS, 2SR)-2-(1-Methyl-2-hydroxy-2-phenylethyl)pyrazine (A) and (1RS, 2RS)-2-phenylethyl)pyrazine (B)

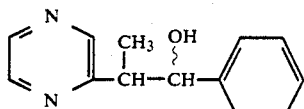

A reaction of ethylpyrazine (10.8 g, 0.1 mole) with benzaldehyde (10.6 g, 0.1 mole) is conducted in accordance with the procedure of Example I. Workup afforded a diastereoisomeric mixture of (A) (R$_f$ 0.25 on silica 4:1 hexane/acetone) and (B) (R$_f$ 0.18). The mixture is separated by centrifugal chromatography using 100:15 hexanes/acetone to yield pure diastereoisomers.

(A): mp 79°-80° C.; $^1$H NMR (CDCl$_3$) δ 1.30 (d, 3H, J = 7.0 Hz), 3.23 (dq, 1H, J = 7.0, 3.5 Hz), 4.19 (d, 1H, J = 2.0 Hz), 5.16 (br t, 1H), 7.38 (br s, 5H), 8.42 (m, 3H).

Anal. Calc. for C$_{13}$H$_{14}$N$_2$O: C,72.87; H,6.59; N,13.08. Found: C,72.82; H,6.66; N,13.05.

(B): mp 58°-59° C., $^1$H NMR (CDCl$_3$) δ 1.28 (d, 3H, J = 7.0 Hz), 3.35 (pentet, 1H, J = 7.0 Hz), 3.70 (d, 1H, J = 5.8 Hz), 5.05 (dd, 1H, J = 7.0, 5.8 Hz), 7.40 (br s, 5H), 8.50-8.68 (m, 3H).

Anal. Calc for C$_{13}$H$_{14}$N$_2$O: C,72.87; H,6.59; N,13.08. Found: C,72.95; H,6.50; N,13.13.

EXAMPLE VII

Preparation Of (R,S)-2-(2-Hydroxy-2-phenylpropyl)pyrazine

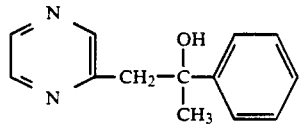

A reaction of 2-methylpyrazine (4.7 g, 0.05 mole) with acetophenone (6.6 g, 0.055 mole) is conducted in accordance with the procedure of Example I. Workup followed by bulb-to-bulb distillation and centrifugal chromatography using 15 hexanes/acetone on silica gel yields 454 mg (4.2%) of the desired product: mp 53°-54° C. (from hexane); $^1$H NMR (CDCl$_3$) δ 1.61 (s, 3H), 3.35 (s, 2H), 5.35 (br s, 1H, 7.18-7.63 (m,5H), 8.38-8.55 (m, 3H).

Anal. Calc. for C$_{13}$H$_{14}$N$_2$O: C,72.87; H,6.59; N,13.08. Found: C,73.03; H,6.58; N,13.04.

EXAMPLE VIII

Preparation Of (R,S)-2-(1,1-Dimethyl-2-hydroxy-2-phenylethyl)pyrazine

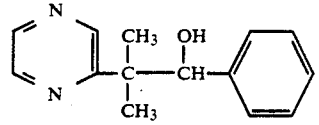

A reaction of isopropylpyrazine (439 mg, 3.6 mmoles) with benzaldehyde (456 mg, 4.33 mmoles) is conducted by means of the Example I procedure with the stirring time extended to 1.5 hours. Workup is followed by bulb-to-bulb distillation [105°-160° C. (oven), 0.01 mm Hg] to give a semi-solid. The resultant material is purified directly by centrifugal chromatography on silica gel using 100:14:3.6 hexanes/acetone/EtOH to yield 177 mg (21%) of product: mp 90°-91° C.; 1.39 (s, 3H), 1.40 (s, 3H), 4.50 (d, 1H, J = 4.5 Hz), 4.95 (d, 1H, J = 4.5 Hz), 7.10-7.12 (m, 2H), 7.24-7.28 (m, 3H), 8.51-8.58 (m, 3H).

Anal. Calc. for C$_{14}$H$_{16}$N$_2$O: C,73.65; H,7.06; N,12.27. Found: C,73.27; H,6.96; N,12.13.

A reaction of tetramethylpyrazine with 3-acetylpyridine yields (R,S)-2-[2-hydroxy-2(3-pyridyl)propyl]-3,5,6-trimethylpyrazine.

EXAMPLE IX

Preparation Of A Mixture Of (1RS,2RS)-2-(1-methyl-2-hydroxy-2phenylpropyl)-pyrazine and (1RS,2SR)-2-(1-methyl-2-hydroxy-2phenylpropyl)-pyrazine

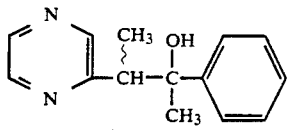

A reaction of ethylpyrazine (5.40 g, 0.05 mole) with acetophenone (6.0 g, 0.05 mole) is conducted in accordance with the previously described procedure. Workup afforded an oil which was crystallized from cyclohexane to yield 3.7 g of the desired product: m.p. 88°–108° C. $^1$H NMR confirms the above structure and indicates about 1:1 mixture of the two diastereoisomers.

Anal. Calc. for $C_{14}H_{16}N_2O$: C,73.65; H,7.06; N,12.27. Found: C,73.60; H,7.20; N,12.19.

A reaction of tetraethylpyrazine with acetophenone yields a 1-position diastereoisomeric mixture of 2-(1-methyl-2-hydroxy-2-phenylpropyl)-3,5,6triethylpyrazines.

EXAMPLE X

Preparation of (R,S)-2-(1,1-dimethyl-2-hydroxy2-phenylpropyl)pyrazine

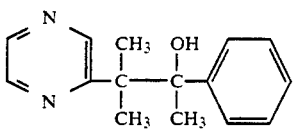

A stirred and cooled (0° C.) solution of 2-(1,1-dimethyl-2-hydroxy-2-phenylethyl)pyrazine (1 g, 4.38 mmoles) in acetone (150 ml) is treated with an aqueous solution of $CrO_3$—$H_2SO_4$ (1.39 ml, 3.72 mmoles). The solution is stirred for 10 minutes, diluted with water (500 ml), allowed to stand for 1 hour and then basified ($Na_2CO_3$). The solution is extracted with $CH_2Cl_2$, and the $CH_2Cl_2$ extracted is dried ($Na_2SO_4$) and concentrated to provide 1.2 g of a turbid oil. Purification by centrifugal chromatography on silica gel and eluting with 100:15:3 hexanes/acetone/EtOH yields 710 mg (71%) of 1-(1-phenyl-2-methyl-2-pyrazinyl)propanone: mp 67°–68° C.; $^1$H NMR (CDCl$_3$) δ 1.73 (s, 6H), 7.23–7.48 (m, 5H), 8.46–8.59 (m, 3H).

Anal. Calc. for $C_{14}H_{14}N_2O$: C,74.31; H,6.24; N,12.38. Found: C,74.22; H,6.10; N,12.23.

A solution of the prepared ketone (390 mg, 1.73 mmoles) in ether (100 ml) is stirred at −70° C. and treated with 2.23 mmoles) of MeLi in ether (2.23 ml). The reaction is quenched with MeOH after being stirred for 2 hours at −65° C. The resultant mixture is concentrated and the residue is taken up in $CH_2Cl_2$, dried ($Na_2SO_4$) and filtered. Purification by centrifugal chromatography on silica gel with 95:4:1 hexanes/acetone/EtOH yields 221 mg (53%) of the desired product: mp 99°–100° C.; $^1$H NMR (CDCl$_3$) δ 1.37 (s, 3H), 1.44 (s, 3H), 1.47 (s, 3H), 5.68 (s, 1H), 7.21–7.34 (m, 5H), 8.48–8.54 (m, 3H).

Anal. Calc. for $C_{15}H_{18}N_2O$: C,74.35; H,7.49; N,11,56. Found: C,74.23; H,7.61; N,11.48.

EXAMPLE XI

Preparation Of (R,S)-2-(1,1-Dimethyl-2-hydroxy-2-phenylethyl)-3-isopropylpyrazine

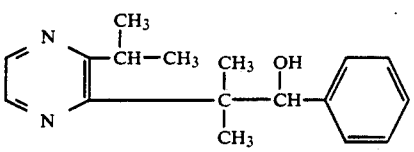

A solution of lithium diisopropylamide in ether is prepared as described in Example I from diisopropylamine (676 mg, 6.7 mmoles) and n-BuLi (6.6 mmoles) in 2.67 ml of hexane at −75° C. The resulting solution is warmed to 0° C. and a solution of 2,3-diisopropylpyrazine (1.0 g, 6.1 mmoles) in ether (2 ml) is added slowly and the reaction mixture is stirred under reflux for 2 hours. The mixture is then treated with benzeldehyde (0.78 g, 7.32 mmoles) as described in Example I.

Workup followed by purification using centrifugal chromatography and recrystallization from hexane affords 10.6 mg (0.64%) of (R,S)-2-(1,1-dimethyl-2-hydroxy-2-phenylethyl)-3-isopropylpyrazine: M.P. 128°–128.5° C.; $^1$H NMR (CDCl$_3$) δ 1.25 (d, 3H, J = 7 Hz), 1.27 (s, 3H), 1.30 (d, 3H, J = 7.0 Hz), 1.48 (s, 3H), 3.59 (heptet, 1H, J = 7.0 Hz), 4.96 (br d, 1H, J = 3.3 Hz, CHOH), 5.28 (br d, 1H, J = 3.3 Hz, CHOH), 7.2–7.4 (m, 5H), 8.31 (d, 1H, J, J = 2.5 Hz), 8.48 (d, 1H, J = 2.5 Hz).

Anal. Calc. for $C_{17}H_{17}N_2O$: C,75.52; H,8.20; N,10.36. Found: C,75.31; H,8.23; N,10.30.

EXAMPLE XII

This Example demonstrates first order rate constants for the pyrolysis of present invention pyrazine compounds in comparison with prior art pyrazine compounds.

The pyrolysis reactions are conducted in diglyme-d$_{14}$ (Merck Sharp & Dohme, Canada, Ltd.) that is dried over a molecular sieve. A 0.4 M solution of each of the pyrazines (0.5 ml) is placed in a thick-walled NMR tube, and the tubes are sealed. Kinetic runs are performed in a constant-temperature oil bath preheated to the desired temperature (170 ± 0.8° C.).

The progress of each pyrolysis is followed by NMR spectroscopy employing a method described in J. Org. Chem. 45, 999 (1980). Percentage compositions are calculated from integration of peaks of both reactants and products mainly in the aromatic regions. In each case the reaction proceeds smoothly with only the parent pyrazine and carbonyl product detected in the reaction mixture. First order rate constants are calculated and the comparative data are summarized in the Table.

The comparative data demonstrate that the heteroaromatic compounds of Examples VIII–X in accordance with the present invention pyrolyze at a significantly higher rate than known heteroaromatic compounds of related structure.

When a present invention heteroaromatic compound is utilized as a smoking composition flavorant-release additive, the fast rate of pyrolysis delivers a high yield of volatile pyrazine and carbonyl components which are effective for enhancement of the flavor and aroma of generated smoke.

TABLE

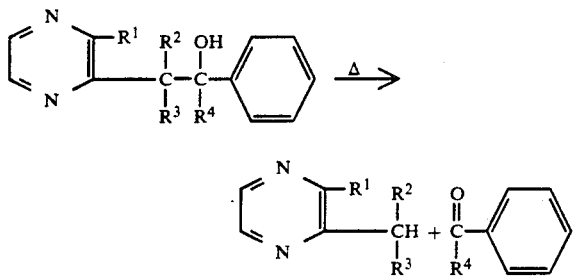

| Example Compound | $R^1$ | $R^2$ | $R^3$ | $R^4$ | $k(sec^{-1}) \times 10$ |
|---|---|---|---|---|---|
| (a)* | H | H | H | H | 1.81 |
| I | $CH_3$ | H | H | H | 9.36 |
| II | $CH_2CH_3$ | H | H | H | 9.49 |
| III | $CH(CH_3)_2$ | H | H | H | 8.69 |
| IV | $CH_2CH(CH_3)_2$ | H | H | H | 9.06 |
| V | $C(CH_3)_3$ | H | H | H | 13.13 |
| VI | H | $CH_3$ | H | H | 5.44 |
|  | H | H | $CH_3$ | H | 4.61 |
| VII | H | H | H | $CH_3$ | 8.91 |
| VIII | H | $CH_3$ | $CH_3$ | H | 53.77 |
| IX | H | $H(CH_3)$ | $CH_3(H)$ | $CH_3$ | 18.57 |
|  | mixture of diastereoisomers | | | | |
| X | H | $CH_3$ | $CH_3$ | $CH_3$ | 426.50 |

*J. Org. Chem., 45, 999(1980).

What is claimed is:

1. A smoking composition comprising an admixture of (1) combustible filler selected from natural tobacco, reconstituted tobacco and tobacco substitutes, and (2) between about 0.0001–5 weight percent, based on the total weight of filler, of a flavorant-release additive corresponding to the formula:

where R is hydrogen or a $C_1$–$C_4$ alkyl group; $R^1$ is hydrogen or a $C_1$–$C_8$ alkyl group; and $R^2$ is a $C_3$–$C_{12}$ aromatic substituent; with the proviso that at least two $R^1$ groups are $C_1$–$C_8$ alkyl radicals.

2. A smoking composition in accordance with claim 1 wherein the $R^2$ substituent in the additive formula is a phenyl radical.

3. A smoking composition in accordance with claim 1 wherein the $R^2$ substituent in the additive formula is a naphthyl radical.

4. A smoking composition in accordance with claim 1 wherein the $R^2$ substituent in the additive formula is a pyridyl radical.

5. A smoking composition in accordance with claim 1 wherein the $R^2$ substituent in the additive formula is a pyrazyl radical.

6. A smoking composition in accordance with claim 1 wherein the $R^2$ substituent in the additive formula is a thiazyl radical.

7. A smoking composition in accordance with claim 1 wherein the $R^2$ substituent in the additive formula is a furyl radical.

8. A smoking composition in accordance with claim 1 wherein the $R^2$ substituent in the additive formula is a thienyl radical.

9. A smoking composition comprising an admixture of (1) combustible filler selected from natural tobacco, reconstituted tobacco and tobacco substitutes, and (2) between about 0.0001–5 weight percent, based on the total weight of filler, of a flavorant-release additive corresponding to the formula:

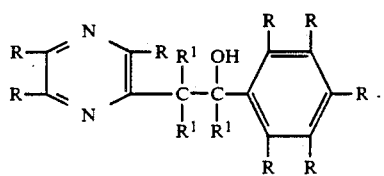

where R is hydrogen or a $C_1$–$C_4$ alkyl group; and $R^1$ is hydrogen or a $C_1$–$C_8$ alkyl group; with the proviso that at least two $R^1$ groups are $C_1$–$C_8$ alkyl radicals.

10. A smoking composition in accordance with claim 9 wherein the flavorant-release additive is 2-(1,1-dimethyl-2-hydroxy-2-phenylethyl)pyrazine.

11. A smoking composition in accordance with claim 9 wherein the flavorant-release additive is 2-(1-methyl-2-hydroxy-2-phenylpropyl)pyrazine.

12. A smoking composition in accordance with claim 9 wherein the flavorant-release additive is 2-(1,1-dimethyl-2-hydroxy-2-phenylpropyl)pyrazine.

13. A pyrazine composition corresponding to the formula:

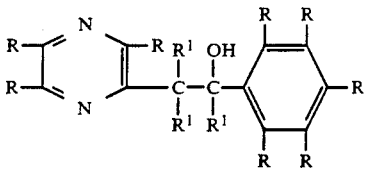

where R is hydrogen or a $C_1$–$C_4$ alkyl group; and $R^1$ is hydrogen or a $C_1$–$C_8$ alkyl group; with the proviso that at least two $R^1$ groups are $C_1$–$C_8$ alkyl radicals.

14. 2-(1,1-Dimethyl-2-hydroxy-2-phenylethyl)-pyrazine.

15. 2-(1-Methyl-2-hydroxy-2-phenylpropyl)-pyrazine.

16. 2-(1,1-dimethyl-2-hydroxy-2-phenylpropyl)-pyrazine.

17. 2-(1,1-Dimethyl-2-hydroxy-2-phenylethyl)-3-isopropylpyrazine.

18. 2-(2-Hydroxy-2-phenylethyl)-3-tertiary-butylpyrazine.

* * * * *